United States Patent [19]

Bergmann et al.

[11] Patent Number: 5,814,461
[45] Date of Patent: Sep. 29, 1998

[54] METHOD FOR THE DETERMINATION OF ANTI-TSH RECEPTOR AUTOANTIBODIES

[75] Inventors: Andreas Bergmann; Joachim Struck; Shaul Kornfeld, all of Berlin, Germany

[73] Assignee: B.R.A.H.M.S. Diagnostica GmbH, Berlin, Germany

[21] Appl. No.: 596,172

[22] PCT Filed: Aug. 18, 1994

[86] PCT No.: PCT/EP94/02748

§ 371 Date: Jul. 9, 1996

§ 102(e) Date: Jul. 9, 1996

[87] PCT Pub. No.: WO95/06258

PCT Pub. Date: Mar. 2, 1995

[30] Foreign Application Priority Data

Aug. 20, 1993 [DE] Germany .......................... 43 28 070.6

[51] Int. Cl.$^6$ ...................... G01N 33/53; G01N 33/536; G01N 33/543; G01N 33/566
[52] U.S. Cl. ...................... 435/7.1; 435/7.93; 435/7.94; 435/7.92; 435/7.95; 436/517; 436/518
[58] Field of Search .................................. 435/7.2, 7.93, 435/7.94, 975, 7.1, 7.92, 7.95; 436/501, 518, 517

[56] References Cited

U.S. PATENT DOCUMENTS

| | | | |
|---|---|---|---|
| 4,447,528 | 5/1984 | Ellis et al. | 435/7 |
| 5,196,513 | 3/1993 | Ryan et al. | 330/327 |
| 5,578,496 | 11/1996 | Atassi et al. | 436/506 |
| 5,614,363 | 3/1997 | Cone | 435/6 |

FOREIGN PATENT DOCUMENTS

| | | |
|---|---|---|
| 147 848 | 7/1985 | European Pat. Off. . |
| 93 00587 | 1/1993 | WIPO . |
| 9322675 | 11/1993 | WIPO . |

OTHER PUBLICATIONS

Smith, et al: "Autoantibodies to the Thyrotropin Receptor", Endocrine Reviews, vol. 9, No. 1, Feb. 1, 1988, pp. 106–121, see the whole document.
Gosling, J. (1990) Clin. Chem. 36: 1408–1427.
Smith et al. (1981) Methods in Enzymology 74: 405–420.

*Primary Examiner*—David L. Fitzgerald
*Assistant Examiner*—Michael Pak
*Attorney, Agent, or Firm*—Cushman Darby & Cushman IP Group of Pillsbury Madison & Sutro LLP

[57] ABSTRACT

Method for the determination of an analyte in a volume of a fluid sample, in particular of anti-TSH receptor autoantibodies in a patient serum, in which one or more determination reagent(s) which contains or which contain a) a predetermined amount of a binder (B) for the analyte (A) and b) a predetermined amount of a competitor (K) which is likewise bound by the binder (B), in such a way that the extent of its binding to the binder (B) is correlated with the simultaneous presence of the analyte (A) and/or its amount in the sample, the competitor (K) being labelled, or being capable of being labelled, with a label which permits its qualitative and/or quantitative determination, is or are added to the sample with the formation of a liquid reaction mixture, wherein c) the liquid reaction mixture is reacted simultaneously or subsequently with a solid phase to which a substance (Imm) for the selective immobilization of the amount of competitor (K) not bound to the binder (B) is bound, and optionally with a labelled reactant (Label) for the immobilized competitor (K), and, after a quantitative separation of the solid phase from the liquid reaction mixture, the amount of the competitor (K) bound to the solid phase is determined in a manner known per se by means of physical and/or chemical detection of the label bound to said competitor, and the determined amount of said competitor (K) is correlated with the presence and/or amount of the analyte (A) in the original sample.

7 Claims, 3 Drawing Sheets

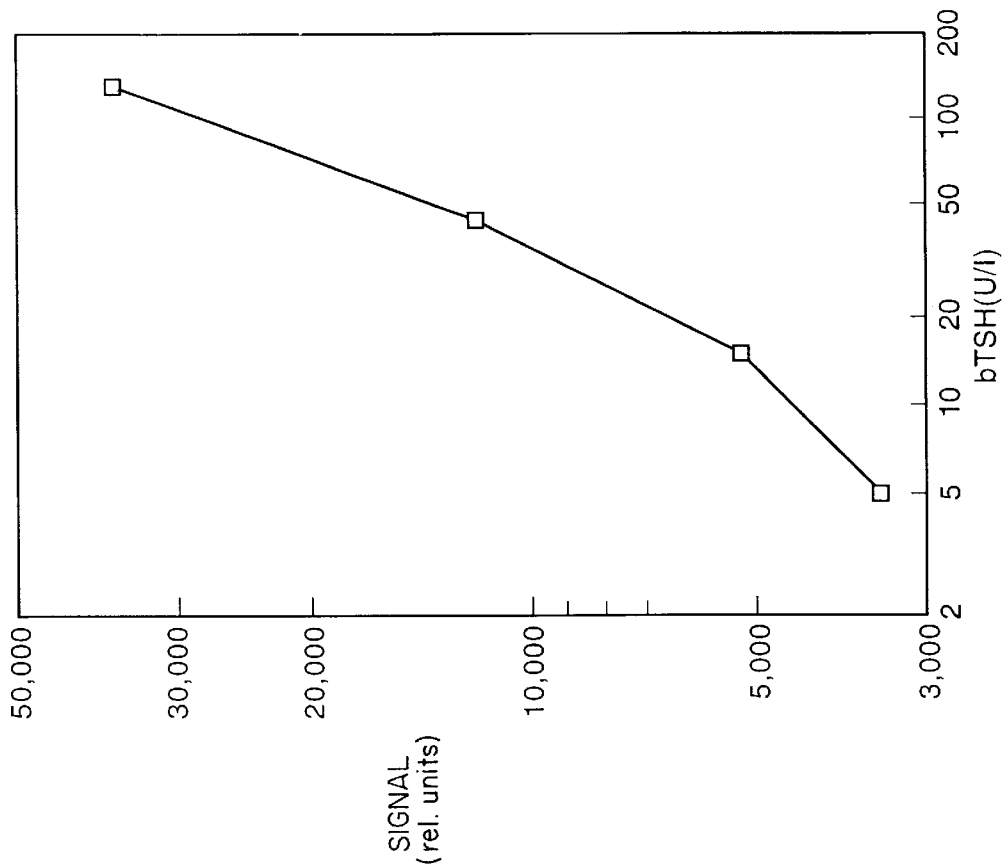
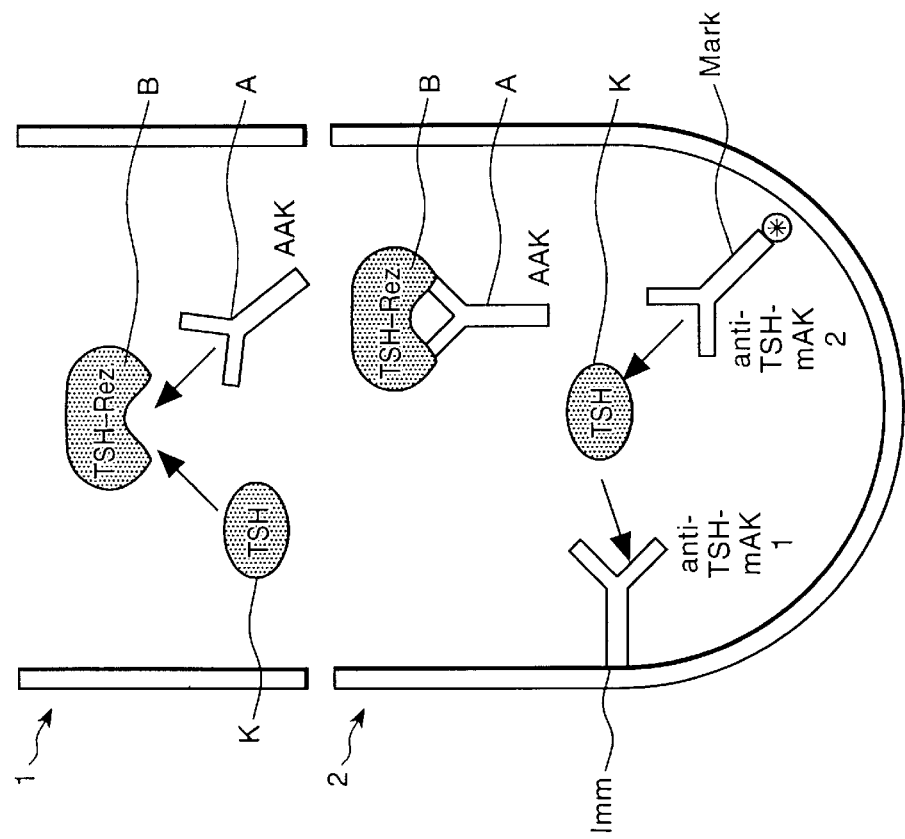

METHOD FOR THE DETERMINATION OF ANTI-TSH RECEPTOR AUTOANTIBODIES

The invention relates to a method for the determination of an analyte in a volume of a fluid sample and its use for the determination of anti-TSH receptor autoantibodies in a patient serum.

An "analyte" in the meaning of the statements relating to the present invention is primarily a biologically active substance, the presence and/or amount of which in a naturally fluid biological sample or in a biological sample converted into fluid form by an appropriate pretreatment are to be determined. In the meaning of the present invention, analytes are therefore primarily substances having hapten or antigen properties, such as hormones, peptide hormones, physiologically active peptides and proteins, the latter also comprising proteins having immunoglobulin character, that is to say antibodies or autoantibodies. The biological samples are primarily blood samples or other fluid blood fractions, such as, in particular, serum samples or plasma samples, but the sample may in principle also be another biological fluid, such as saliva or urine, or solubilized tissue extracts. However, the invention is not restricted to the determination of biologically active substances of natural origin but also includes the determination of medicaments and their metabolites in biological fluids and can also be used for the determination of any other substances in any fluids if the use of the relatively expensive method according to the present invention is useful for the determination of such analytes and the binding partners and reactants required in such a case for carrying out the method according to the invention can be found. However, the present invention is particularly important for the determination of biologically active substances, in particular of substances of a protein nature, in biological fluids, and in turn for the determination of those analytes which are difficult to determine in another manner known per se. Where the determination method according to the invention is described below primarily with reference to certain types of analytes or even with reference to certain analytes, this is not to be interpreted to imply a restriction of the method according to the invention to such analytes.

While a wide range of chemical and/or physical methods of determination are available for simple chemical substances of inorganic or organic nature, biologically active analytes, in particular naturally occurring biological molecules having certain physiological functions, must, as a rule, be determined by so-called immunodiagnostic methods since, owing to their nature and/or the amount in which they occur, other methods of determination cannot be used or, for example, are too expensive for clinical practice.

It may be assumed that such immunological methods of determination are in principle known. The known methods can be assigned to various types, depending on the reaction type, the substance to be determined or the detection method to be used. Thus, some of the methods can be assigned to so-called competitive determinations, which include the classical radioimmunoassay (RIA) and which, depending on the label, the type of molecule to be determined and the determination in homogeneous or heterogeneous phase, can in turn be assigned to various subtypes. Regarding the basic method for the determination of antigens and antibodies by competitive methods, reference may be made, for example, to the top of column 3 of US-B1-3654090. In this method, a known amount of a competitor and less than the required amount of a specific binder are added to the sample to be investigated, as a rule one of the components, competitor or binder, being present in labelled form and the other in immobilized form, and the desired amount of the analyte is determined from the amount of the label bound to the solid phase. In this method, it is thus necessary for at least one of the components, binder or competitor, to be capable of being immobilized and the other to be capable of being labelled, the possibility of subsequent indirect labelling also being sufficient instead of direct labelling.

Another principle, which is known as the so-called sandwich determination method, is suitable for analytes which have two different binding sites for binders, such as, for example, different antibodies. First, the total amount of analyte present in the sample is bound by means of an excess of a first immobilized antibody, and this amount is labelled subsequently or simultaneously with a second labelled antibody. In indirect variants of this principle, as are realized, for example, in EP-A1-0105714 or EP-A1-147848, a further immobilized or labelled antibody is used either for immobilizing or for labelling the sandwich containing the analyte to be determined. In all these methods, the analyte to be determined is finally itself present in the immobilized and labelled immunocomplex, which is obtained as a result of the assay and is measured.

In their various embodiments, the above basic methods can be used for the determination of most biologically active analytes in biological fluids.

However, there is a number of cases in which, for various reasons, including availability, achievable purity, stability, immobilizability and binding properties of the reactants reacted with one another in the method of determination, the known principles are not directly applicable or entail a number of serious disadvantages in their application, which at first glance make more complicated modifications of the classical methods of determination appear more advantageous than the simple basic methods. An example of such a more complex method of determination is described in German Patent 4,120,412 (WO-A-93005872) of the Applicant, in which, for the reasons described in detail in the is stated patent, the determination of autoantibodies against human thyroid peroxidase (hTPO) is carried out in such a way that the disturbance of the synthesis of the sandwich from components belonging to the assay kit <->, is measured. <by the analytes present in the sample, that is to say by autoantibodies against hTPO> In this method, the presence of the analyte to be determined manifests itself as a reduction in the binding of a label to a solid phase. A substantial advantage of the stated process is that it is possible to dispense with the high purification, previously regarded as essential, of the antigen hTPO, which serves as a competitor to the anti-hTPO antibodies.

Problems of a somewhat different type may occur in particular in cases where one of the reactants of the method of determination is a receptor. The binding of biological molecules of a peptide or protein nature to receptors is, as a rule, very complex, and the formation of a bond between receptor and biological molecule is very much more sensitive to structural changes of the biological molecule or of the receptor, for example as a result of labelling or of immobilization, than is the case with a conventional antigen/antibody binding pair. For the feasibility of the known immunological methods of determination according to one of the basic principles described above, this results in there being only slight freedom with regard to the design of such a method. Thus, in the case of the determination of anti-TSH receptor autoantibodies, it has not been possible to date to employ immobilized receptors (and labelled bTSH) or immobilized competitors (and labelled receptor).

The statements just made are to be explained in further detail for the case of the determination of autoantibodies against the TSH receptor, which is also a preferred case for carrying out a typical method of determination according to the present invention.

TSH is a pituitary hormone which plays a key role in regulating the function of the thyroid. Its release is stimulated by the hormone TRH formed in the hypothalamus and controls the formation and release of the most important thyroid hormone thyroxine (T4). On the basis of a feedback, the thyroxine content of the serum controls the release of TSH. The formation of thyroxine by the thyroid cells is stimulated by TSH by a procedure in which the TSH released by the pituitary binds to the TSH receptor of the thyroid cell membrane.

In certain pathological conditions, various types of autoantibodies against this TSH receptor can also be formed. Depending on the type of these autoantibodies, either inhibition of the formation and release of thyroxine may occur at the TSH receptors owing to the shielding of the TSH molecules, or, on the other hand, this thyroid hormone may be released in an uncontrolled manner because the anti-TSH receptor autoantibodies mimic the action of the TSH and stimulate the synthesis and release of thyroid hormones. The thyroid hormone excess resulting in the latter case manifests itself, inter alia, as hyperthyroidism of the Grave's disease type.

The detection of anti-TSH receptor autoantibodies is thus very important for clinical practice, and there is already a number of known radioreceptor assays which permit the determination of such autoantibodies in biological fluids.

Such TSH receptor assays function similarly to competitive radioimmunoassays, except that, instead of anti-analyte antibodies, preparations of TSH receptors are used as specific binding reagent for the autoantibodies to be determined and the TSH preparation used as a competitor in radiolabelled form. Owing to the peculiarities of the receptor/TSH interaction which are further explained below, the test must be carried out so that the reaction of the TSH receptor preparation with the radiolabelled TSH preparation and the sample is carried out in the liquid phase, and the reaction products formed from receptor and binding partners are precipitated, for example by the addition of polyethylene glycol, and, after removal of the supernatant, the radioactivity in the pelletized precipitate is measured.

The basic principles and details of the known determination of anti-TSH receptor autoantibodies in human serum are described in many publications, among which, in addition to the product information of the various test manufacturers, the articles by L. C. Harrison and P. J. Leedman in Clin. Biochem. Vol. 23, pages 43 to 48, 1990, Bernard Rees Smith et al., in Endocrine Reviews, Volume 9, No. 1, pages 106 to 121, 1989, and Bernard Rees Smith and Reginald Hall, Methods in Enzymology, Volume 74, pages 405 to 420, 1981, may be mentioned in particular. All receptor assays described for the determination of anti-TSH receptor autoantibodies realize the basic method described above. Regarding further details, reference may be made to the content of the non-prior-published German Patent Application P 42 37 430.8 of the Applicant. Receptor assays intended for the determination of anti-TSH receptor autoantibodies and operating according to a basic principle other than that described above have not been disclosed to date.

The reason for this is the nature of the interaction receptor/autoantibody or receptor/labelled TSH preparation. This has so far made it impossible, for example, to use the TSH receptor in immobilized form and to measure the radioactivity to be measured at the solid phase after a conventional liquid/solid separation, and furthermore labelling of the receptor preparation and its reaction with an immobilized TSH preparation as competitor to the analyte has not proved feasible to date. Moreover, labelling of the TSH preparation with labels other than radioactive ones has not been possible in practice to date. Thus, for example, the radioactive label cannot be replaced by an enzyme label or a fluorescent label since these would be either concomitantly precipitated or deactivated in the required precipitation of the receptor/binding partner complexes. Moreover, the receptor binding capacity of known TSH preparations is impaired too greatly and uncontrollably by the attempt to add bulky organic radicals as a label.

Previous receptor assays for the determination of anti-TSH receptor autoantibodies were therefore inevitably radioreceptor assays of the precipitation type, although such assays have a number of disadvantages for the user as well as for the producer, namely:

1. Exclusively radioactive methods have the known safety burdens for producer, user and environment.

2. The centrifuging required for bound/free separation for pelletizing the precipitate is substantially more time-consuming and inconvenient to handle than other methods now very widely used in immunodiagnostics, such as, for example, the coated tube and microtitre plate technology.

3. The production of the radiolabelled TSH as a tracer is expensive and technically difficult. First, the generally bovine TSH obtained from natural sources must be purified by an expensive multistage procedure, which results in a decrease in the specific receptor binding activity. The required subsequent oxidative radioiodination reduces the binding activity further.

4. The efficiency of the precipitation and the unspecific pelletization of the tracer are also dependent, inter alia, on the composition of the sample. However, the latter varies with different patient sera, so that the actual measured values may be falsified with this test design.

Among the advantages of the known method is that endogenous human TSH present in the serum sample does not interfere with the binding of the bovine TSH to the porcine TSH receptor generally used. The affinity of bovine TSH to porcine TSH receptor is the greatest of all investigated combinations of TSH/TSH receptor of different biological origin, so that it is desirable to make use of these advantages in newly designed tests too.

It is the object of the present invention to provide a novel method for the determination of an analyte in a volume of a liquid sample, in particular a method which is of the receptor assay type, in which, with regard to the nature of the competitor for an analyte to be determined and the method for its labelling, there is a greater independence of the test from the nature of the analyte and of the associated binder, and which makes it possible in particular to provide receptor assays which can manage without a precipitation step and can function with almost any label.

It is a particular object of the present invention to provide a method for the determination of anti-TSH receptor autoantibodies which functions according to such a novel principle and is free of the above-mentioned disadvantages of the known method but simultaneously retains its advantages.

These objects are achieved by methods of determination according to Claim 1 and the embodiment of this method according to Claim 15.

Advantageous embodiments of these methods are described in the subordinate subclaims.

Further preferred embodiments and features of the basic method and its specific design for the determination of anti-TSH receptor autoantibodies are evident from the following description.

For an explanation and illustration of the basic principle of the method, reference may be made to FIG. 1.

The method according to the invention achieves the basic object by a procedure in which the presence and amount of the analyte (A) to be determined is indirectly measured by carrying out the actual concentration measurement as a measurement of the concentration of the immobilized competitor (K) which is not bound to the binder (B) and is directly labelled or can be labelled with an additional antibody (Label), in particular with formation of an immobilized sandwich, and the amount of which is correlated with the amount of the analyte (A) in the sample to be investigated, in such a way that an increased content of analyte (A) leads to an increased amount of bound competitor (K) or bound label (Label).

Since, in the method according to the invention, it is not necessary for the label to be present in the complex comprising binder, for example receptor, and competitor, but labelling may be effected independently of a complex comprising binder/analyte or competitor, any restriction with regard to the applicability of certain labels can be avoided in the method according to the invention.

Owing to the indirect determination of the analyte via a determination of a competitor not directly bound to the binder, the requirements with regard to the purity and other binding properties of the test reagents binder and competitor can be reduced. In order for the test to function, all that is primarily required is that the extent of the binding of the competitor to the binder, for example the receptor, is sufficiently clearly influenced by the presence of the analyte to be determined—this requirement is, as a rule, met only if the binder is a specific binder, for example also a receptor; and that the unbound constituents of the competitor can be immobilized in such a way that simultaneous immobilization and/or labelling of those constituents of the competitor which are bound to the binder do not occur and the binding of the competitor to the binder is not significantly impaired by the immobilization of the unbound amounts of competitor.

In other words, the binding of the competitor (for example of the bovine TSH in the determination of anti-TSH receptor autoantibodies) to the binder (TSH receptor) must be sufficiently favoured in comparison with the binding of the competitor to the solid phase, that is to say the complex formed by interaction of binder and receptor must be sufficiently thermodynamically and/or kinetically stable so that there is no significant liberation of the already bound competitor from the stated complex in the presence of the substance used for the selective immobilization of the competitor, within the common incubation times used. This can be achieved through the correct choice of the concentrations of the test components and/or the staggering and the duration of the incubations for the various reactions and/or the choice of antibodies which have sufficiently low association kinetics for the immobilization and labelling of the competitor not bound to the binder, or by working under conditions which lead to such association kinetics.

Furthermore, it must be ensured that the label bound to the solid phase is actually only a label of the competitor not bound to the binder. In other words, it is necessary to prevent a) antibodies or antibody fragments used for subsequent labelling of the competitor from binding directly to the antibodies immobilized on the solid phase for immobilization of the competitor, and b) furthermore the complexes of binder and competitor from being bound to the solid phase or, if they are to be bound, from being labelled. The last-mentioned requirement is fulfilled when at least one of the two antibodies used for immobilizing and labelling the competitor binds to an epitope of the competitor (bTSh) which is blocked by the preferential binding of the competitor to the binder (of the bTSH to the porcine TSH receptor).

Of course, the competitor and the binder must be used as test components in amounts such that there is effective competition of the competitor with the analyte for the binding sites of the binder. However, it is not necessary for the competitor and the analyte to compete directly for the same binding site; instead, it is sufficient for the binding of the competitor to be reduced in a clear manner by the binding of the analyte to the binder. This results in a higher proportion of unbound competitor in the fluid phase, which proportion reflects the concentration of the analyte in the fluid reaction mixture and can therefore be subsequently determined by binding to a solid phase and labelling.

Owing to the proportionality between antibody concentration and competitor not bound to the binder but immobilized on the solid phase and labelled, the method according to the invention permits a quantitative measurement of the concentration of the analyte in the fluid sample, and of course, as is usual in such tests, a measured value is compared with a calibration curve prepared using calibration substances.

The method can, however, also be carried out as a simple qualitative positive/negative test by using relatively small amounts of binder and competitor, so that complete displacement of the competitor from the binder is likely at the analyte concentrations to be expected in the sample, and the resulting, more or less constant signal of the immobilized competitor represents a signal for "presence of the analyte".

That the above various requirements with regard to the components of the method of determination can be realized in practice is shown by the following specific embodiment for carrying out this method as a method for the determination of anti-TSH receptor autoantibodies.

In connection with the description of the stated specific method, reference is made to figures. which show the following:

FIG. 1 is a schematic representation of the basic method according to the invention, with its required test components for the example of the determination of anti-TSH receptor autoantibodies;

FIG. 2 shows the binding of a labelled TSH antibody to a solid phase coated with another TSH antibody and in the form of a wall of a test tube, said binding being dependent on the concentration of an added bTSH;

Figure 6:
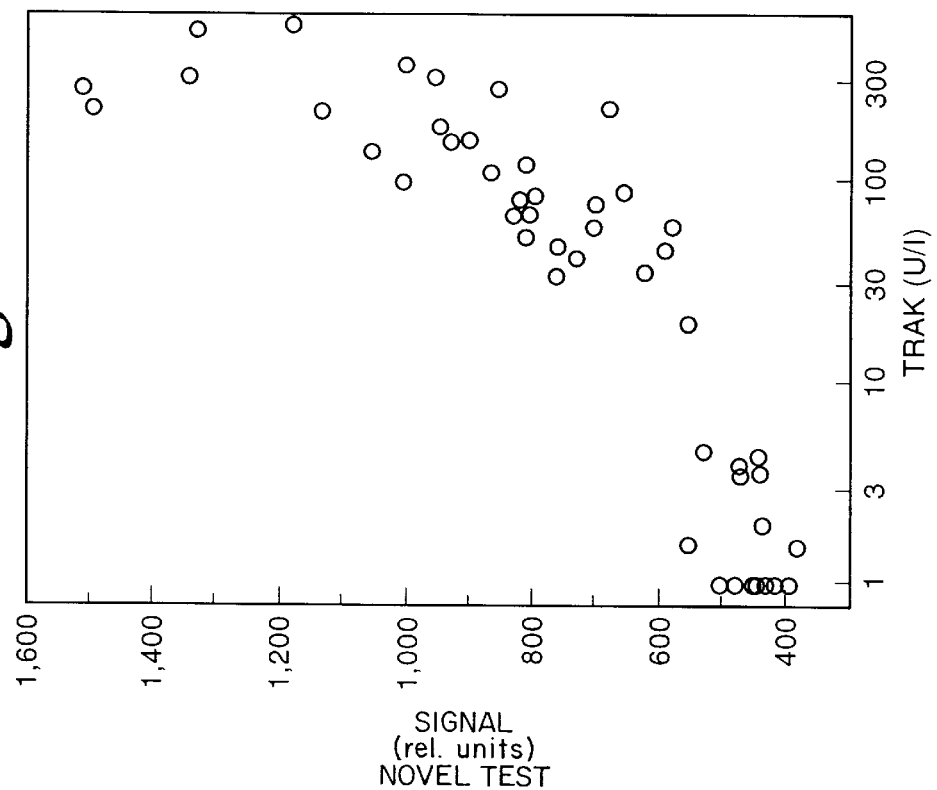
Figure 5:
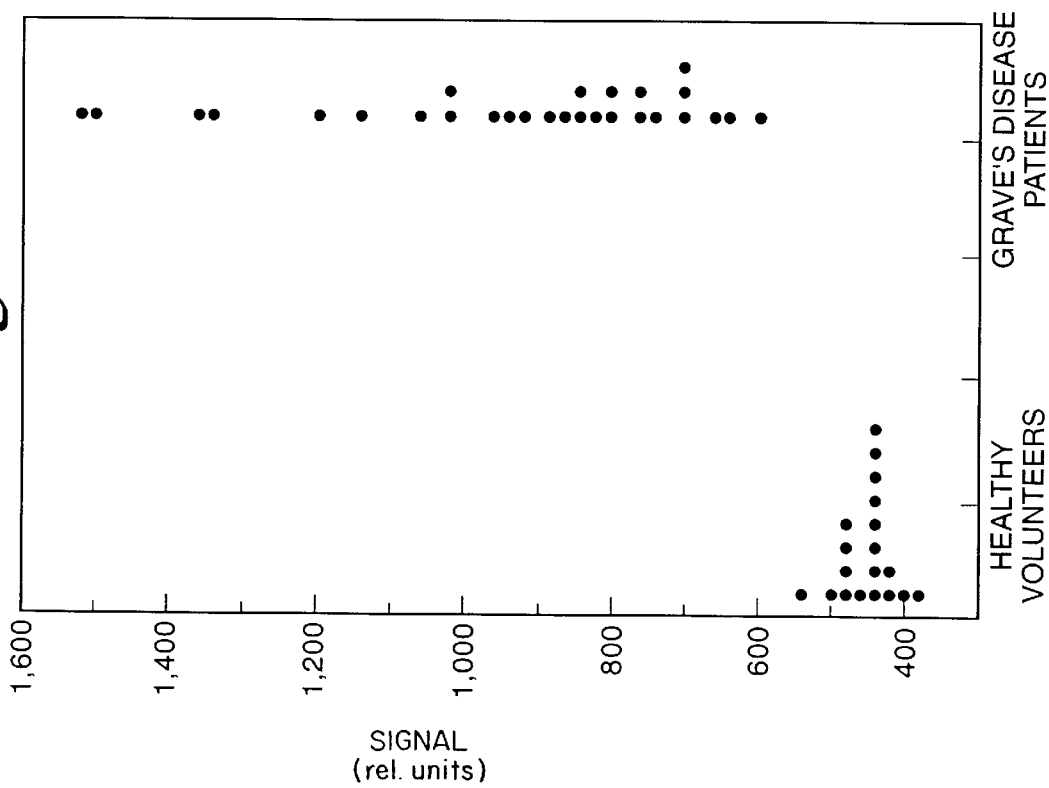

FIG. 5 shows the results of a measurement of serum groups of patients suffering from Grave's disease and healthy volunteers by a method according to the invention, and FIG. 6 shows a correlation of the measured values obtained by the method according to the invention with the measured values of a traditional test for the determination of anti-TSH receptor autoantibodies which has been tested in practice.

To examine the question as to whether anti-TSH receptor autoantibodies can be determined in practice by a method of determination according to the invention, various tests were carried out using the following materials and methods.

Material and methods

1. Test tubes

For the preparation of a solid phase for immobilizing bTSH used as the competitor, polystyrene star tubes (NUNC) were coated with 1.0 μg of monoclonal, commercially available anti-TSH antibodies (antibody No. 5405 from Medix, Finland) per 300 μl of 0.1M NaHCO$_3$, pH 8.0 (15 hours, room temperature), after which saturation and freeze-drying were carried out in a manner known per se with 0.5% bovine serum albumin (BSA)/3% Karion/0.005% NaN$_3$.

According to the producer, the special anti-TSH antibody is specific for hTSH or the beta-subunit of hTSH and has an affinity constant of 5×10$^9$ l/mol hTSH. It is produced in vitro and is commercially available as an affinity-purified Ig fraction in 0.15 mol/l NaCl with a content of 0.1% NaN$_3$ (protein concentration 0.02 mg/ml).

2. Bovine TSH preparation used as competitor

A commercial TSH preparation with the name "Thytropar" from Rorer Pharmaceuticals was used in an amount of 100 μU per determination.

3. Porcine TSH receptor used as binder

A porcine TSH receptor which is a crude detergent extract of porcine thyroid membranes and the preparation of which is described in the literature (cf. for example Bernard Rees Smith and Hall in Meth. Enzym. 74, pages 405 to 420, 1981, or Patent Application P 42 37 430.8 of the Applicant) was used. The porcine TSH receptor was used in a concentration four times higher than that of conventional known methods of determination.

4. Labelled antibody for labelling an immobilized bTSH competitor

A commercial monoclonal mouse anti-bTSH antibody which is known to bind bTSH in a different epitope from the antibody used for coating the test tubes (monoclonal anti-bTSH antibody 920831-52 from CLB, Amsterdam, The Netherlands) was labelled by known methods with acridinium ester in a molar ratio of 1:1. Acridinium ester label not bound to the antibody was separated off by gel filtration. For carrying out the test, the tracer obtained was adjusted to a concentration of 200000 RLU (Relative Light Units) per 200 μl of 10 mM tris/HCl pH 7.5/0.1% BSA/0.4 mg/ml mouse IgG/0.4 mg/ml bovine IgG.

It is assumed that the use of this stated antibody is just as uncritical as the use of the first-mentioned one. The suitablility of other possible monoclonal antibody pairs obtainable in a manner known per se by immunization (for example with bTSH) of test animals and subsequent conventional selection can be simply tested in the manner described in tests 1 and 2 below.

The following tests were carried out using the above materials:

Test 1

In a preliminary test, it was determined whether a bTSH sandwich bound to a solid phase can be prepared using the monoclonal antibodies used for coating the test tubes and for preparing the tracer. For this purpose, various amounts of bovine TSH were incubated together with 200000 RLU of the tracer prepared as above in a volume of 300 μl of PBS (phosphate-buffered saline solution) in the test tubes prepared as described above, while shaking at 300 rpm. The bound/free separation was then carried out in a manner known per se and the solid-phase luminescence was measured. The luminescence bound to the test tubes was measured with an LP 952 T luminometer from Bertold.

FIG. 2 shows that increasing amounts of tracer are immobilized with increasing amounts of bTSH, that is to say a sandwich can be prepared using the two selected antibodies.

Test 2:

Testing of the effect of the presence of a TSH receptor preparation on the amount of bovine TSH measurable in the "sandwich" reaction according to test 1.

The following procedure was used:

1. Variable amounts of crude porcine TSH receptor (50 μl, from TSH receptor reagent TRAK-Assay Henning Berlin) were pipetted into the test tubes coated with monoclonal anti-TSH antibodies.

2. 25 μl of bovine TSH (Thytropar, Rorer, 100 μU in PBS) were then pipetted.

3. 200 μl of labelled monoclonal anti-TSH antibodies (luminescence-labelled; 200000 RLU in PBS) were then added by means of a pipette.

Incubation was then carried out for two hours while shaking at 300 rpm and at room temperature, after which the bound/free separation, washing of the solid phase and measurement of the luminescence bound to the solid phase were carried out as in FIG. 1.

Figure 3:
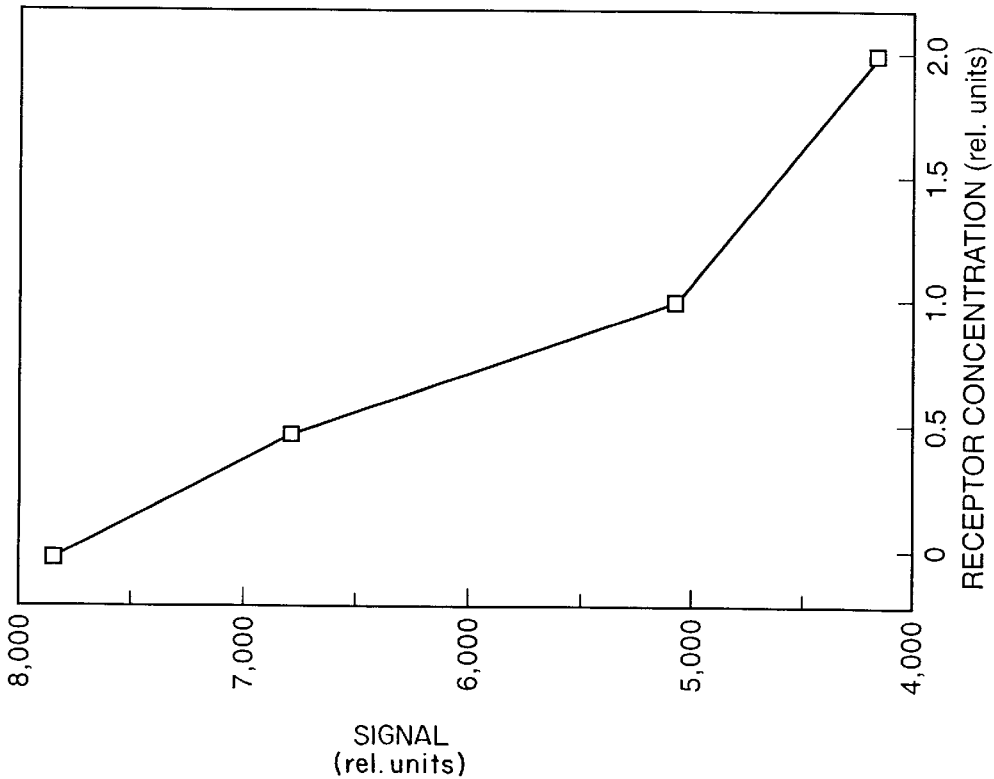
FIG. 3 shows the reduction in the measured signal in the system according to FIG. 2 in the case of preincubation with a porcine TSH receptor.

As shown in FIG. 3, the presence of the porcine TSH receptor preparation leads to a reduction in the amount of bTSH which can be labelled and immobilized on the solid phase, which shows that the amount of bTSH in the solution was reduced as a result of binding to the added receptor.

Test 3:

Defined amounts of anti-TSH receptor autoantibodies were added to the test system according to test 2. One autoantibody concentration unit corresponds to a serum with an antibody titre of 350 U/l. Such a serum was diluted with an antibody-free serum, and added to the reagent system according to test 2.

Specifically, the complete test, which can be carried out in this form both for calibrating with known samples and for measuring unknown samples, was carried out as follows: The following were first pipetted into uncoated test tubes; 50 μl of the porcine TSH receptor and 50 μl of the antibody-containing serum sample.

This was followed by incubation for fifteen minutes at room temperature. 25 μl of bTSH (100 μU) were then added by means of a pipette.

After incubation for one hour at room temperature, 100 μl of the liquid reaction mixture were transferred to the coated test tubes which had been coated with the monoclonal anti-TSH antibody 5405, and 200 μl of the second anti-bTSH antibody labelled with the acridinium ester were added to produce the sandwich.

Incubation was carried out for three hours at room temperature while shaking at 300 rpm and washing was carried out with the use of a commercial Lumitest wash solution from Henning Berlin. The luminescence bound to the test tubes was then measured as in test 1, using the LB 952 T luminometer from Bertold.

Figure 4:
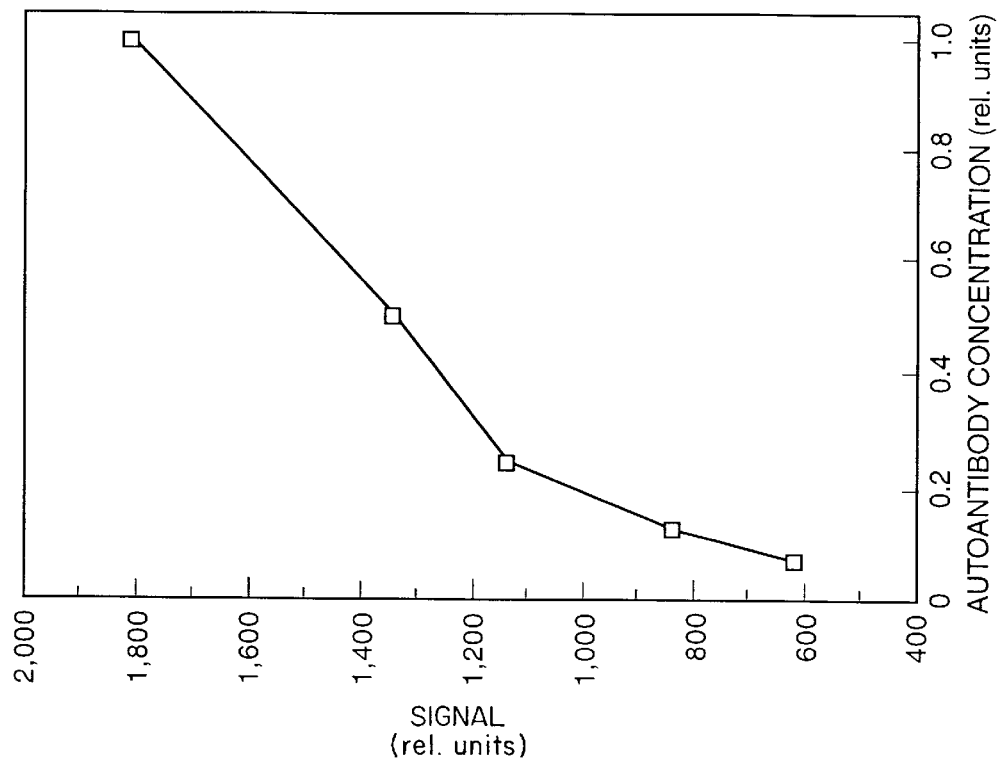
FIG. 4 shows the elimination of the receptor-related reduction of the measured signal according to FIG. 3 by the addition of patient serum with anti-TSH receptor autoantibodies, increasing amounts of immobilized and labelled bTSH corresponding to increasing amounts of autoantibodies.

FIG. 4 shows the increase in the concentration of the luminescent label bound to the wall of the test tube as a function of the amounts of added anti-TSH receptor autoantibody.

Test 4:

For the determination of the clinical usefulness, sera whose donors are classified as having Grave's disease were measured by the method of determination according to the invention, according to the incubation protocol described under test 3. In addition, sera from people with healthy thyroids who were free of anti-TSH autoantibodies were measured.

FIG. 5 clearly shows that a clear distinction between healthy volunteers and patients suffering from Grave's disease is possible by the method according to the invention.

The values obtained in the measurement of the antibody-containing sera by the method according to the invention were furthermore compared with the results of measurements by an acknowledged comparison method used in practice (TRAK-Assay of Henning Berlin).

The results are shown in FIG. 6. It can be seen that the results of the method according to the invention can be correlated with the results obtained by the known method of determination. autoantibody-free, negative sera (<15 U/l) give low measured values in the test according to the invention as in the known test, while autoantibody-containing, positive sera generally give higher measured values even in the method of determination according to the invention. The results shown in FIG. 6 document the clinical usefulness of the novel method of determination in the practical embodiment described.

In the method of determination described above, the binder (crude porcine TSH receptor from porcine thyroids) is preincubated with the sample (patient serum) and the competitor (crude bovine TSH) in a test tube.

The liquid reaction mixture is then transferred to a test tube which has a coating for selective binding of those constituents of the competitor which are not bound to the binder (coating with a monoclonal anti-bTSH antibody), and at the same time the second, labelled antibody (luminescence-labelled monoclonal anti-bTSH antibody) is added to the tube. This antibody is chosen so that it does not bind to the competitor bound by the binder (bTSH bound to the receptor) or to the second anti-bTSH antibody immobilized on the test tube wall.

After the incubation, washing is carried out and the luminescence on the tube wall is measured. The amount of bTSH thus detected is proportional to the amount of the analyte in the patient sample.

The reaction procedure described can however be varied specifically with regard to the concentration of the components, pipetting sequence, etc.

Compared with the method of determination described at the outset for anti-TSH receptor autoantibodies, the method according to the invention has the following advantages:

1. For use in the test according to the invention, the bovine TSH used as competitor need be neither purified nor labelled and instead the bovine TSH extracted in one step from bovine pituitary as crude homogenate can be used. This reduces the danger of a loss of activity as a result of specific purification and labelling steps, and a maximum specific receptor binding activity is ensured.

2. In contrast to the known methods, the bound/free separation is effected not by centrifuging but by simple, conventional washing of the test tubes. This is faster, more economical and more convenient and is thus a considerable handling advantage for the user.

The restriction on the use of radioactive labels which exists in the known test is absent in the method according to the invention. Since the competitor need not be directly labelled, there is no need to take into account the impairment of the receptor binding activity of the competitor. The labelling of an antibody as a tracer is very much less problematic than the labelling of bTSH as competitor. The interaction of an antibody with an antigen takes place with participation of only a small part of the antibody, with the result that a large part of the antibody can be chemically changed without this influencing its immunoreactivity. On the other hand, the receptor binding is very much more complex and very much more sensitive to external effects, as may be produced by the introduction of a label.

4. Since no centrifuging is carried out in the method according to the invention, there are no related measurement errors which are attributable, for example, to different protein concentrations in the samples to be measured and an associated unspecific pelletization of the tracer and which may occur in the known method.

We claim:

1. A method for detecting anti-TSH receptor autoantibody in a fluid sample, which method comprises:

(A) contacting a solid phase, said solid phase having bound to it a first monoclonal anti-TSH antibody, with a solution which comprises said sample and which further comprises:
 (1) a TSH receptor preparation,
 (2) a TSH preparation, under conditions such that
  Anti-TSH receptor autoantibody in said sample, if any, binds to TSH receptor in said TSH receptor preparation, thereby reducing the extent of binding of TSH to said TSH receptor compared to the extent of binding of TSH to said TSH receptor under the same conditions in the absence of anti-TSH receptor autoantibody, and
  said first monoclonal anti-TSH antibody specifically binds TSH not bound to said TSH receptor in said TSH receptor preparation, (B) determining the amount of TSH immobilized by said first monoclonal anti-TSH antibody by determining the amount of said TSH bound to said solid phase, and (C) correlating the amount of TSH immobilized by said first monoclonal anti-TSH antibody, if any, in the presence of said sample with the amount of TSH immobilized by said first monoclonal anti-TSH antibody under the same conditions in the absence of anti-TSH receptor, autoantibody, whereby anti-TSH receptor autoantibody in said sample, if any, is detected.

2. A method for determining the amount of anti-TSH receptor autoantibody in a fluid sample, which method comprises:

(A) contacting a solid phase, said solid phase having bound to it a first monoclonal anti-TSH antibody, with a solution which comprises said sample and which further comprises:
 (1) a TSH receptor preparation,
 (2) a TSH preparation, under conditions such that
 anti-TSH receptor autoantibody in said sample, if any, binds to TSH receptor in said TSH receptor preparation, thereby reducing the extent of binding of TSH to said TSH receptor compared to the extent of binding of TSH to said TSH receptor under the same conditions in the absence of anti-TSH receptor autoantibody, and
 said first monoclonal anti-TSH antibody specifically binds TSH not bound to said TSH receptor in said TSH receptor preparation, (B) determining the amount of TSH immobilized by said first monoclonal anti-TSH antibody by determining the amount of said TSH bound to said solid phase, and (C) correlating the amount of TSH immobilized by said first monoclonal anti-TSH antibody, if any, in the presence of said sample with the amount of TSH immobilized by said first monoclonal anti-TSH antibody under the same conditions in the absence of anti-TSH receptor, autoantibody, whereby anti-TSH receptor autoantibody in said sample, if any, in said sample is determined.

3. A method according to claim 1 or 2 wherein said TSH receptor preparation is a porcine TSH receptor preparation and said TSH preparation is a bovine TSH preparation.

4. A method according to claim 3 wherein said porcine TSH receptor preparation is in the form of a crude extract of porcine thyroid membranes and said bovine TSH preparation is in the form of a crude extract of bovine tissue.

5. A method according to claim 1 or 2 wherein said TSH bound to said solid phase is detected with a labeled second monoclonal anti-TSH antibody or a fragment thereof which binds to said immobilized TSH but not to said solid phase.

6. A method according to claim 5 wherein said second labeled monoclonal anti-TSH antibody or fragment thereof is labeled with a label selected from the group consisting of a radioactive isotope, an enzyme, a substrate of an enzyme reaction, a fluorescent label and a chemiluminescent label.

7. A method according to claim 1 or 2 wherein said TSH is directly labeled with a radioactive isotope and said TSH bound to said solid phase is detected by detecting said radioactive isotope bound to said solid phase.

* * * * *